United States Patent
Lian et al.

(10) Patent No.: US 8,380,307 B2
(45) Date of Patent: Feb. 19, 2013

(54) SWITCH POLARITY PACING TO IMPROVE CARDIAC RESYNCHRONIZATION THERAPY

(75) Inventors: Jie Lian, Beaverton, OR (US); Garth Garner, Tigard, OR (US); Dirk Muessig, West Linn, OR (US); Volker Lang, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 1051 days.

(21) Appl. No.: 12/255,516

(22) Filed: Oct. 21, 2008

(65) Prior Publication Data
US 2009/0240298 A1 Sep. 24, 2009

Related U.S. Application Data

(60) Provisional application No. 61/037,335, filed on Mar. 18, 2008.

(51) Int. Cl.
*A61N 1/00* (2006.01)
(52) U.S. Cl. .......................................................... 607/9
(58) Field of Classification Search ................. 607/9, 28, 607/74, 148
See application file for complete search history.

(56) References Cited

U.S. PATENT DOCUMENTS

| | | | |
|---|---|---|---|
| 5,800,464 A | 9/1998 | Kieval | |
| 5,815,079 A | 9/1998 | Getman et al. | |
| 6,342,232 B1 | 1/2002 | Loosmore et al. | |
| 6,343,232 B1 * | 1/2002 | Mower | 607/9 |
| 6,829,506 B2 | 12/2004 | Pastore et al. | |
| 7,319,900 B2 * | 1/2008 | Kim et al. | 607/27 |
| 7,680,536 B2 * | 3/2010 | Sathaye et al. | 607/28 |
| 7,908,003 B1 * | 3/2011 | Mower | 607/9 |
| 2003/0120313 A1 * | 6/2003 | Begemann et al. | 607/9 |
| 2005/0055058 A1 | 3/2005 | Mower | |

* cited by examiner

*Primary Examiner* — Mark W Bockelman
(74) *Attorney, Agent, or Firm* — ARC IP Law, PC; Joseph J. Mayo

(57) ABSTRACT

The invention is directed to a heart stimulator for left-ventricular pacing comprising a left ventricular stimulation pulse generator connected or connectable to a single electrode lead for left ventricular stimulation having one or more electrodes for delivery of stimulation pulses to left ventricular myocardial heart tissue, said stimulation pulse generator being adapted to generate and deliver stimulation pulses of switchable polarity. The heart stimulator further comprises a control unit connected to the stimulation pulse generator for controlling the stimulation pulse generator and to trigger generation and delivery of stimulation pulses having a polarity controlled by said control unit, wherein the control unit is adapted to control said left ventricular stimulation pulse generator so as to deliver at least a pair of suprathreshold stimulation pulses of opposite polarity.

14 Claims, 2 Drawing Sheets

SWITCH POLARITY PACING TO IMPROVE CARDIAC RESYNCHRONIZATION THERAPY

This application takes priority from U.S. Provisional Patent Application Ser. No. 61/037,335, filed 18 Mar. 2008, the specification of which is hereby incorporated herein by reference.

BACKGROUND OF THE INVENTION

1. Field of the Invention

The present invention generally relates to implantable cardiac devices, including pacemakers, defibrillators and cardioverters, which stimulate cardiac tissue electrically to control the patient's heart rhythm. More particularly, the present invention relates to a method and apparatus for a three-chamber implantable pacemaker or defibrillator to treat heart failure with cardiac dyssynchrony.

2. Description of the Related Art

Cardiac resynchronization therapy (CRT) is a proven technique for treating drug refractory heart failure (HF) with cardiac dyssynchrony. By delivering properly timed left ventricular (LV) pacing, CRT can pre-excite the LV region that otherwise would show delayed activation, thus correcting the intra-ventricular dyssynchrony. In addition, by delivering properly timed right ventricular (RV) pacing with respect to the LV pacing, the inter-ventricular dyssynchrony can also be corrected. Improving the intra-ventricular and inter-ventricular synchrony, CRT can effectively improve the hemodynamic performance of the heart, leading to improvement in cardiac contractility and cardiac output. Growing evidence suggests that CRT can result in reverse remodelling of the heart, manifested by reduced mitral regurgitation, reduced end-systolic and end-diastolic volume of the LV, and improved ejection fraction (EF). Consequently, CRT has been shown to improve the longevity and quality of life of the HF patients.

However, despite its great success, clinical experience has shown that about one third of the CRT candidates are non-respondents. There are many possible explanations for the non-responsiveness, including inappropriate LV lead location, non-optimal A-V delay and V-V delay settings, etc. Particularly, the inappropriate LV lead location is considered one of the most important factors that contribute to reduced CRT efficacy. Preferably, the LV pacing should pre-excite the LV myocardium with the most delayed intrinsic activation. However, in many cases, due to the difficulty to implant the LV lead through the coronary sinus, the LV lead could not be placed in such target location. As a result, the LV pacing could not correct the delayed LV activation of that region, thus the intra-ventricular dyssynchrony remains. In other circumstances where patient has ischemic heart disease, the LV pacing electrode may overlay or near the myocardial infarct region which either does not respond to LV pacing or could not conduct properly the electrical activation.

To solve this problem, several approaches have been attempted on multi-site LV pacing, based on the concept that simultaneous activation of larger myocardial volume could improve the intra-ventricular synchrony. For example, Lenarczyk et al. investigated the feasibility of triple-site (double LV and single RV) pacing for treating HF patients. The response rate after 3 months triple-site CRT was higher than 95%. Recently, Yoshida et al. examined the effect of CRT by triangle ventricular (Tri-V) pacing at RV apex, RV outflow tract, and the LV. In acute settings, they showed that Tri-V significantly improved HF patients' LV function with better resynchronization effects compared with conventional biventricular pacing. Multi-site LV pacing system was also disclosed in U.S. Pat. Appl. No. 2005/0055058 by Mower. In addition, a method and apparatus for linear stimulation of the heart using an elongated electrode or plurality of electrodes were also disclosed in U.S. Pat. No. 6,829,506 issued to Pastore et al. However, implantation of multiple leads is technically challenging, requires longer procedure duration and fluoroscopy time, and may lead to higher complication rate. Design of CRT system with multiple electrodes for LV pacing not only requires special lead design, but also requires fundamental change of the hardware and firmware of the implant device.

Although conventional cardiac pacing uses cathodal stimulation, it has been shown that anodal stimulation can also reliably depolarize the cardiac tissue. The underlying mechanism has been explained by the virtual electrode theory. On one hand, a strong, short anodal pacing pulse can hyperpolarize a "dog bone" shaped region of the myocardial tissue underlying the stimulation electrode (virtual anode). On the other hand, depolarization can occur at virtual cathodes adjacent to the virtual anode (a,k.a., anodal make stimulation).

Virtual electrode theory has been used to examine the basic mechanisms of cardiac pacing such as the factors affecting the stimulation threshold and pace/shock termination of ventricular tachyarrhythmia. Recently, several clinical observations on cardiac pacing have also been explained by the virtual electrode theory. Tedrow et al. and Sauer et al. independently showed that increasing LV pacing amplitude can produce a larger virtual electrode, which can result in capture of a larger myocardial area, and reduce the conduction time from LV to RV. Lloyd et al. demonstrated that CRT with anodal LV pacing can significantly improve the LV function compared to conventional CRT with cathodal LV pacing. The underlying mechanism was thought to be larger area of direct activation by the virtual cathode than the cathodal pacing.

Anodal stimulation has also been suggested for implantable pacing systems. For example, in U.S. Pat. No. 5,800,464 issued to Kieval, it was disclosed that properly timed sub-threshold anodal stimulation might hyperpolarize the myocardial cells of a heart chamber to enhance the relaxation thereof in the diastolic phase and to thereby enhance cardiac function. In U.S. Pat. No. 5,814,079 also issued to Kieval, it was further disclosed that the properly timed anodal stimulation might prevent cardiac arrhythmia by suppressing aberrant electrical activity, and might also convert the detected tachyarrhythmia. However, these hypotheses have never been supported by clinical evidence. In addition, the so-called proper timing and proper strength of the anodal stimulation as required in above patents are not easy to maintain in the implantable pacing device. In U.S. Pat. No. 6,342,232 and U.S. Pat. App. No. 2005/0055058 both issued to Mower, a biphasic stimulation method was disclosed, whereby a sub-threshold anodal stimulation is applied followed by a cathodal stimulation. The subthreshold anodal stimulation, by hyperpolarizing the cardiac cells, acts as a conditioning mechanism to improve conduction through the heart muscle. Evidently, the sub-threshold anodal stimulation was never intended for myocardial capture. The increase of conduction speed in the local myocardial sites by anodal pacing does not necessarily translate to improvement in cardiac mechanical synchrony or cardiac function.

In view of above, there is a need for an implantable cardiac pacing system that can depolarize multiple regions of the heart nearly simultaneously to improve the effectiveness of the CRT.

BRIEF SUMMARY OF THE INVENTION

According to this invention, an apparatus and a method are provided for an implantable cardiac device to achieve switch polarity pacing (SWAP).

In a preferred embodiment, an anodal left ventricular stimulation pulse is delivered first to capture a left ventricular region distant to an left ventricular electrode (LV electrode), then immediately a cathodal left ventricular stimulation pulse is delivered to capture a left ventricular region adjacent to the LV electrode. Optionally, an additional anodal pacing pulse is delivered before the cathodal pacing using another LV electrode to capture a different left ventricular region distant to the LV electrode.

Note, that for the purpose of this description, the terms "pacing", "pacing pulse" and "stimulation pulse" are used as synonyms.

According to the present invention, the pacing strength of the anodal pacing can be adjusted to affect the size of the virtual cathode. Also according to this invention, for both anodal pacing and cathodal pacing, the cathode and anode can be respectively selected from a plurality of electrodes to form different pacing vectors, which can capture different areas of the heart. The electrode pairs that are selected for anodal pacing and cathodal pacing are those that correspond to maximal improvement of the cardiac function.

It is believed by the inventors that, by switching between anodal pacing and cathodal pacing, it is possible to achieve multi-site capture of the LV through a single LV lead. By selecting proper electrodes for anodal pacing and cathodal pacing and by adjusting the pacing amplitude, the SWAP can nearly simultaneously activate a larger myocardial area, which may include the site with most delayed intrinsic activation while beyond the region of myocardial infarction or conduction block. Consequently, the SWAP can potentially reduce intra-ventricular dyssynchrony, and improve hemodynamic function of the heart.

It is also believed by the inventors that the SWAP can minimize the proarrhythmic risk that was reported in anodal pacing alone. The anodal pacing depolarizes the myocardial site that is distant to the pacing electrode while hyperpolarizing the local myocardial site. The immediately following cathodal pacing also activates the local myocardial site, rendering it refractory to further depolarization. Thus SWAP can nearly simultaneously generate two activation waves, preventing the formation of reentry circuit.

In particular, the objective of the invention is achieved by a heart stimulator for left-ventricular pacing that comprises a left ventricular stimulation pulse generator that is connected or can be connected to a single left ventricular electrode lead adapted to be placed for left ventricular stimulation and having one or more electrodes for delivery of stimulation pulses to left ventricular myocardial heart tissue. The stimulation pulse generator is adapted to generate and deliver stimulation pulses of switchable polarity. The heart stimulator further comprises a control unit that is connected to said stimulation pulse generator for controlling said stimulation pulse generator and for triggering generation and delivery of stimulation pulses having a polarity controlled by said control unit. The control unit is further adapted to control said left ventricular stimulation pulse generator so as to deliver at least a pair of supra-threshold stimulation pulses of opposite polarity.

Likewise, the objective of the invention is achieved by a method for stimulating the left ventricle of a heart by means of electrical stimulation pulses, wherein the method comprising the steps of delivery of a first anodal stimulation pulse to the left ventricular myocardium immediately followed by a delivery of a second cathodal stimulation pulse to the left ventricular myocardium, and wherein both the anodal stimulation pulse and the cathodal stimulation pulse are suprathreshold stimulation pulses, meaning each has a pulse strength sufficient to cause capture of the myocardium.

According to a preferred embodiment, the control unit is adapted to control the left ventricular stimulation pulse generator so as to first deliver at least one anodal stimulation pulse via an electrode on said left ventricular electrode lead and to deliver a cathodal stimulation pulse via the same or a different electrode on said left ventricular electrode lead immediately following the anodal stimulation pulse.

According to a further preferred embodiment, the left ventricular stimulation lead comprises a left ventricular tip electrode and said control unit is adapted to select said left ventricular tip electrode as anode (positive electrode) for anodal pacing.

Alternatively, if the left ventricular stimulation lead comprises a left ventricular ring electrode, the control unit may be adapted to select said left ventricular ring electrode as anode for anodal pacing.

Regarding the last two aspects, it is preferred that the heart stimulator comprises or is connected to further electrodes other than the left ventricular tip electrode or the left ventricular ring electrode, and the control unit is adapted to select one of said further electrode as cathode for anodal pacing. The further electrode acting as cathode for anodal pacing can be one of: an electrically conducting part of a heart stimulator's housing (device can IMD-CASE), a coil electrode adapted for placement in the superior vena cava (SVC), a coil electrode adapted for placement in the right ventricle, or the combination of said coil electrode adapted for placement in the superior vena cava (SVC) and said coil electrode adapted for placement in the right ventricle.

Regarding the pulse strength of the anodal stimulation pulse, the control unit is preferably adapted to control the left ventricular stimulation pulse generator so as to deliver an anodal stimulation pulse having a strength that is selected so that on one hand, the anodal pacing alone results in left ventricular capture, whereas on the other hand, it does not result in cathodal capture of the right ventricle or phrenic nerve stimulation.

Regarding delivery of the cathodal stimulation pulse following the anodal stimulation pulse, the control unit is preferably adapted to select the left ventricular ring electrode or the left ventricular tip electrode as cathode for cathodal pacing.

Preferably, the control unit is adapted to select a further electrode as anode for cathodal pacing, wherein said further electrode acting as anode for cathodal pacing can be one of: an electrically conducting part of a heart stimulator's housing (device can, IMD-CASE), a coil electrode adapted for placement in the superior vena cava (SVC), a coil electrode adapted for placement in the right ventricle, or the combination of said coil electrode adapted for placement in the superior vena cava (SVC) and said coil electrode adapted for placement in the right ventricle.

Regarding the pulse strength of the cathodal stimulation pulse following the anodal stimulatiuon pulse, it is preferred that the control unit is adapted to control the left ventricular stimulation pulse generator so as to deliver a cathodal stimulation pulse having a strength that is selected so that on one hand, the cathodal pacing alone results in left ventricular capture, whereas on the other hand, it does not result in anodal capture of the right ventricle or phrenic nerve stimulation.

According to a further preferred embodiment, the control unit is adapted to control the left ventricular stimulation pulse generator so as to first deliver more than one anodal stimulation pulse via an electrode on said left ventricular electrode lead and to deliver a cathodal stimulation pulse via the same or a different electrode on said left ventricular electrode lead immediately following the last anodal stimulation pulse.

In the latter case, it is preferred that the control unit is adapted to control the left ventricular stimulation pulse generator so as to deliver more than one anodal stimulation pulse wherein a second anodal stimulation pulse is delivered using an electrode configuration different from the electrode configuration used for delivery of the first anodal stimulation pulse. In a typical embodiment, the control unit is adapted to control the left ventricular stimulation pulse generator so that the first anodal stimulation pulse is delivered between a left ventricular ring electrode acting as anode and a right ventricular coil electrode acting as cathode, the second anodal stimulation pulse is delivered between the left ventricular tip electrode acting as anode and an electrically conducting housing of the heart stimulator acting as cathode, and the following cathodal stimulation pulse is delivered between the left ventricular tip electrode acting as cathode and the left ventricular ring electrode acting as anode.

BRIEF DESCRIPTION OF THE DRAWINGS

The details of the invention can be understood from the following drawings and the corresponding text descriptions.

DETAILED DESCRIPTION OF THE INVENTION

Figure 1:
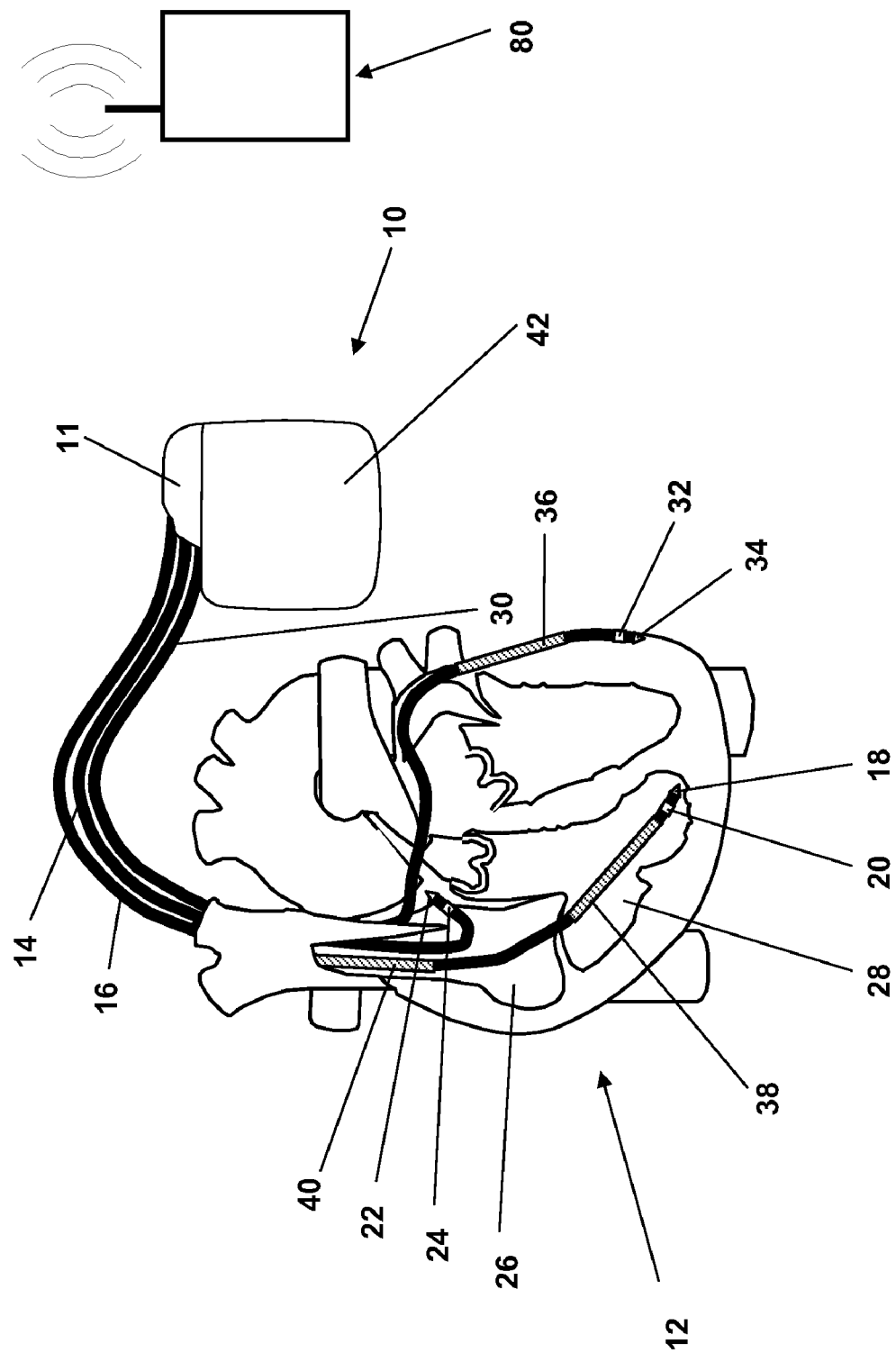
FIG. 1 illustrates the heart stimulator connected to electrode leads that are placed in a heart together with an external device.
Figure 2:
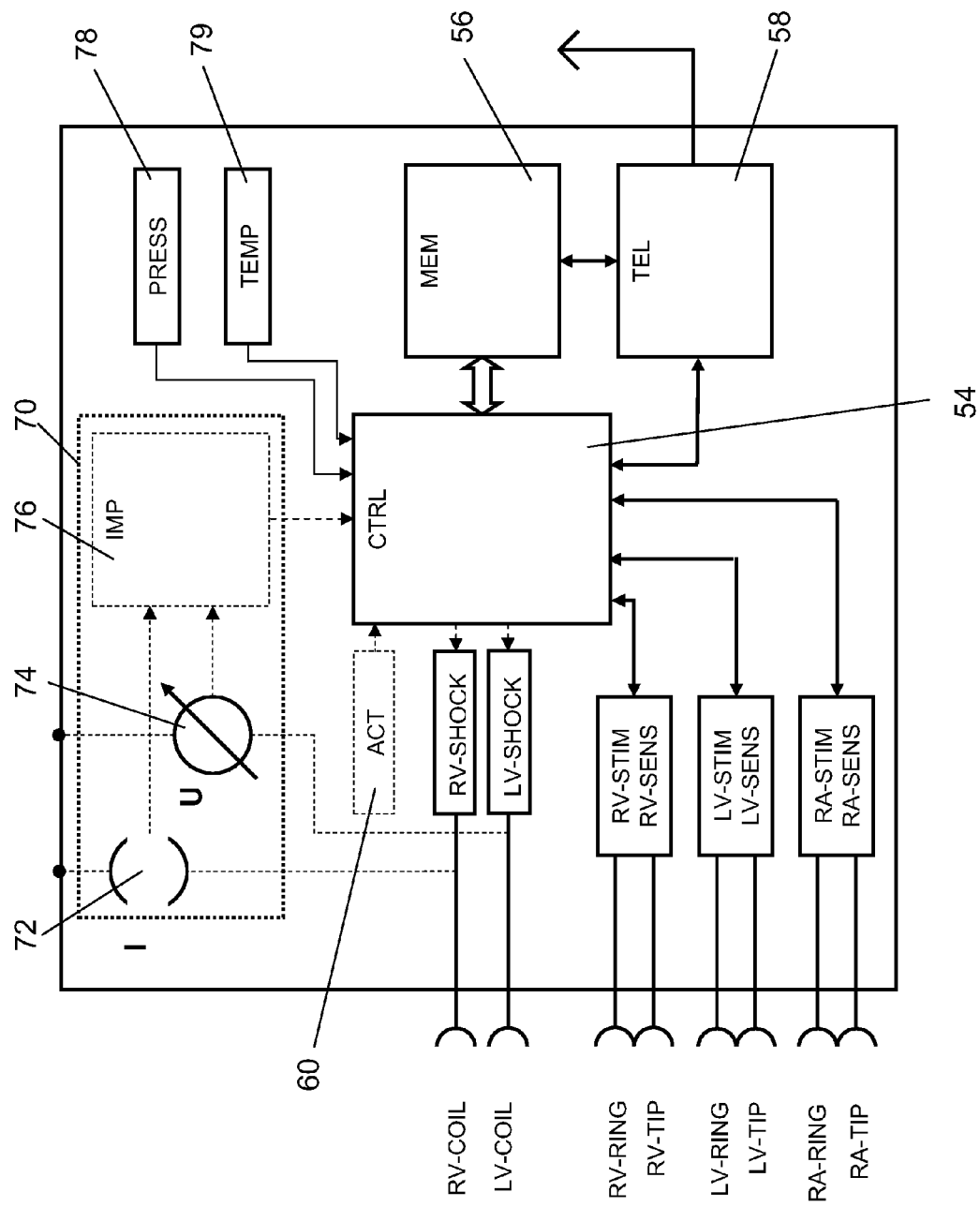
FIG. 2 shows a schematic block diagram of the heart stimulator of FIG. 1.

A typical implantable medical device is an implantable heart stimulator as illustrated with respect to FIGS. 1 and 2.

In FIG. 1 the implantable medical device is a three chamber biventricular pacemaker and cardioverter/defibrillator 10 that is connected to pacing/sensing leads placed in a heart 12 is illustrated.

Pacemaker 10 comprises a gas proof housing (can) 42 made from a biocompatible metal such as titanium. Pacemaker 10 comprises a transparent header 11 that is made from electrically insulating plastic and that encloses terminals to which electrode leads 16, 14 and 30 are connected detachably. Electrode leads 16, 14 and 30 each comprise a proximal connector (not shown) that is plugged into the connectors of header 11.

The implantable medical device 10 is electrically coupled to heart 12 by way of leads 14, 16 and 30.

Lead 14 is a right atrial electrode lead that has a pair of right atrial electrodes 22 and 24 that are in contact with the right atrium 26 of the heart 12.

Lead 16 is a right ventricular electrode lead that has a pair of ventricular stimulation and sensing electrodes 18 and 20 that are in contact with the right ventricle 28 of heart 12. Further, a right ventricular defibrillation shock coil RV-COIL 38 and an atrial defibrillation shock coil SVC-COIL 40 are arranged on lead 16.

Electrodes 22 and 18 are tip electrodes at the very distal end of leads 14 and 16, respectively. Electrode 22 is a right atrial tip electrode RA-TIP and electrode 18 is a right ventricular tip electrode RV-TIP. Electrodes 24 and 20 are ring electrodes in close proximity but electrically isolated from the respective tip electrodes 22 and 18. Electrode 24 forms a right atrial ring electrode RA-RING and electrode 20 forms a right ventricular ring electrode RV-RING. Atrial defibrillation shock coil SVC-COIL 40 and right ventricular defibrillation shock coil RV-COIL 38 are coil electrodes providing a relatively large geometric area when compared to the stimulation electrodes 18, 20, 22 and 24.

Lead 30 is a left ventricular electrode lead passing through the coronary sinus of heart 12 and having a left ventricular ring electrode LV-RING 32 a left ventricular tip electrode LV-TIP 34. Further, a left ventricular defibrillation shock coil LV-COIL 36 is arranged on lead 30.

Implantable medical device 10 has a case (can) 42 made from electrically conductive material such as titanium that can serve as a large surface electrode IMD CASE.

The plurality of electrodes 18, 20, 22, 24, 32, 34, 36, 38 and 40 connected to implantable medical device 10 together with case 42 allow for a number of different electrode configurations for sensing, pacing, as well as measuring intrathoracic and intracardiac impedance.

Referring to FIG. 2 a simplified block diagram of an implantable medical device 10 is illustrated. During operation of the pacemaker leads 14, 16 and 30 are connected to respective output/input terminals of pacemaker 10 as indicated in FIG. 2 and carry stimulating pulses to the tip electrodes 18, 22 and 34 from a right ventricular pulse generator RV-STIM, a right atrial stimulation pulse generator RA-STIM and a left ventricular pulse generator LV-STIM, respectively. On demand, defibrillation pulses will be provided from right ventricular shock generator RV-SHOCK, left ventricular shock generator LV-SHOCK and atrial shock generator RA-SHOCK (not shown) to right ventricular defibrillation shock coil RV-COIL 38, left ventricular shock coil LV-COIL 36 and an atrial defibrillation shock coil SVC-COIL 40 (not shown), respectively. Further, electrical signals from the right ventricle are carried from the electrode pair 18 and 20, through the lead 16, to the input terminal of a right ventricular sensing stage RV-SENS; and electrical signals from the right atrium are carried from the electrode pair 22 and 24, through the lead 14, to the input terminal of a right atrial channel sensing stage RA-SENS. Electrical signals from the left ventricle are carried from the electrode pair 32 and 34, through the lead 30, to the input terminal of a right ventricular sensing stage RV-SENS.

The atrial channel sensing stage RA-SENS and ventricular sensing stages RV-SENS and LV-SENS comprise analog to digital converters (ADC; not shown) that generate digital signals from electric signals picked up in the atrium or the ventricles, respectively.

Controlling the implantable medical device 10 is a control unit CTRL 54 that is connected to sensing stages RA-SENS, RV-SENS and LV-SENS, to stimulation pulse generators RA-STIM, RV-STIM and LV-STIM and to an impedance determination unit 70. Control unit CTRL 54 comprises a digital microprocessor forming a central processing unit (CPU; not shown) and is—at least in part—controlled by a program stored in a memory circuit MEM 56 that is coupled to the control unit CTRL 54 over a suitable data/address bus ADR.

Control unit CTRL 54 receives the output signals from the atrial sensing stage RA-SENS and from the ventricular sensing stages RV-SENS and LV-SENS. The output signals of sensing stages RA-SENS and RV-SENS are generated each time that a P-wave representing an intrinsic atrial event or an R-wave representing an intrinsic ventricular event, respectively, is sensed within the heart 12. An As-signal is generated, when the atrial sensing stage RA-SENS detects a P-wave and a Vs-signal is generated, when the ventricular sensing stage RV-SENS detects an R-wave.

Control unit CTRL 54 also generates trigger signals that are sent to the atrial stimulation pulse generator RA-STIM and the ventricular stimulation pulse generators RV-STIM and LV-STIM, respectively. These trigger signals are generated each time that a stimulation pulse is to be generated by the respective pulse generator RA-STIM, RV-STIM or LV-STIM. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, RA-SENS, RV-SENS and/or LV-SENS, is typically disabled by way of a blanking signal presented to these amplifiers from the control unit CTRL 54, respectively. This blanking action prevents the sensing stages RA-SENS, RV-SENS and LV-SENS from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

In order to successfully stimulate a heart chamber, a stimulation pulse needs to have strength above capture threshold of that heart chamber. Stimulation pulse strength can be altered by changing the amplitude and/or the pulse with of a stimulation pulse. Control unit CTRL 54 and stimulation pulse generators RA-STIM, RV-STIM and LV-STIM are adapted to adjust the pulse strength of stimulation pulses in order to provide stimulation pulses that have a strength sufficient to cause capture, yet without requiring excessive energy in order to avoid unnecessary depletion of the pacemaker's battery.

Control unit 54 is also connected to pulse generators RV-SHOCK, LV-SHOCK and RA-SHOCK (not shown) to control the delivery of high energy pulses for defibrillation, if necessary.

How the stimulation pulses are to be delivered according to this invention is disclosed in more details hereinafter.

Control unit CTRL 54 comprises circuitry for timing ventricular and/or atrial stimulation pulses according to an adequate stimulation rate that can be adapted to a patient's hemodynamic need as pointed out below.

Basic timing intervals, among others, are an atrioventricular delay (AV-delay, AVD) between an atrial event and a scheduled right ventricular stimulation pulse and an interventricular delay (VV-delay, VVD) between a right ventricular event and the subsequent left ventricular stimulation pulse, or between a left ventricular event and the subsequent right ventricular stimulation pulse. These and other timing intervals such as an atrial or a ventricular escape interval are controlled by control unit CTRL 54.

Still referring to FIG. 2, the implantable medical device 10 includes a memory circuit MEM 56 that is coupled to the control unit CTRL 54 over a suitable data/address bus ADR. This memory circuit MEM 56 allows certain control parameters, used by the control unit CTRL 54 in controlling the operation of the implantable medical device 10, to be programmably stored and modified, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 56 for later retrieval and analysis.

A telemetry circuit TEL 58 is further included in the implantable medical device 10. This telemetry circuit TEL 58 is connected to the control unit CTRL 54 by way of a suitable command/data bus. Telemetry circuit TEL 58 allows for wireless data exchange between the implantable medical device 10 and an external device 80 or some remote programming or analyzing device which can be part of a centralized service center serving multiple pacemakers.

The implantable medical device 10 in FIG. 2 is referred to as a three chamber pace-maker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage RA-SENSE, the atrial stimulation pulse generator RA-STIM and corresponding portions of the control unit CTRL 54, are commonly referred to as the atrial channel. Similarly, those portions of the pacemaker 10 that interface with the right ventricle 28, e.g., the lead 16, the R-wave sensing stage RV-SENSE, the ventricular stimulation pulse generator RV-STIM, and corresponding portions of the control unit CTRL 54, are commonly referred to as the right ventricular channel. Likewise, those portions of the pacemaker 10 that interface with the left ventricle, e.g. the lead 30, the sensing stage LV-SENS, the left ventricular stimulation pulse generator LV-STIM, and corresponding portions of the control unit CTRL 54, are commonly referred to as the left ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 60 that is connected to the control unit CTRL 54 of the pacemaker 10. While this sensor ACT 60 is illustrated in FIG. 2 as being included within the pacemaker 10, it is to be understood that the sensor may also be external to the implantable medical device 10, yet still be implanted within or carried by the patient. A common type of sensor is an accelerometer, such as a piezoelectric crystal, mounted to the case of the pacemaker. Other types of physiologic sensors are also known, such as sensors that sense the oxygen content of blood, respiration rate, blood pH, intra-cardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient.

The control unit CTRL 54 is adapted to determine an adequate heart rate or stimulation rate in any manner known as such.

For impedance measurement, an impedance determination unit 70 is provided. Impedance determination unit 70 comprises a constant current source 72 that is connected or can be connected to electrodes for intracorporeal placement as shown in FIG. 1. In order to allow for a plurality of impedance measurement electrode configurations, preferably some means of switching is provided between the constant current source 72 and the electrode terminals of the implantable medical device 10. The switch is not shown in FIG. 2. Rather, particular impedance measurement configurations are shown as examples.

Similarly, an impedance measuring unit 74 for measuring a voltage corresponding to a current fed through a body by said constant current source is provided and can be connected to a number of electrodes although a switch for switching between these configurations is not shown in FIG. 2.

As an alternative to constant current source 72 a constant voltage source can be provided. Then, the measuring unit will be adapted to measure a current strength of a current fed through a body by said constant voltage source.

Both, constant current source 72 and impedance measurement unit 74, are connected to an impedance value determination unit 76 that is adapted to determine an impedance value for each measuring current pulse delivered by the constant current source 72.

The impedance value determination unit 76 comprises another analog to digital converter ADC in order to generate a digital impedance signal that is fed to the control unit CTRL 54.

Further, a pressure sensor PRESS 78 for sensing a pressure in the interior of housing 42 and a temperature sensor TEMP 79 for sensing a temperature in housing 42 are provided. Both sensors 78 and 79 are connected to control unit CTRL 54 via an analog to digital converter.

Control unit CTRL 54 further comprises watchdog and reset units (not shown) to provide safety when the CPU should fail. The watchdog units therefore are designed to operate independently from the CPU of the control unit CTRL 54.

Now the details of switch polarity pacing as controlled by control unit 54 shall be explained with respect to left ventricular pacing in the course of cardiac resynchronisation therapy (CRT). It is to be understood, that the basic principles underlying left ventricular switch polarity pacing generally can also be applied to stimulation of another heart chamber, in particular to stimulation of the right ventricle.

In a preferred embodiment, control unit 54 controls LV pacing to be a stimulation sequence that consists of two pacing pulses: an anodal stimulation immediately followed by a cathodal stimulation. Both pacing pulses have suprathreshold strength, that is, either anodal pacing or cathodal pacing can independently capture the LV.

Now first consider the anodal stimulation. In one embodiment, the anodal pacing is delivered by selecting the LV-TIP electrode as the anode, that is, the relatively positive stimulation electrode. In another embodiment, the anodal pacing is delivered by selecting the LV ring electrode as the anode. In both embodiments, the cathode, that is, the corresponding relatively negative stimulation electrode, can be selected from a plurality of electrodes, including but not limited to, the device can IMD-CASE formed by an electrically conducting part of a heart stimulator's housing 42, the SVC-COIL 40, the RV-COIL 38, or the combined SVC-RV coils.

Different combinations of above said electrodes can form different spatial vectors for the anodal pacing, thus the location of the virtual cathode generated by the anodal pacing may also vary. Consequently, the anodal pacing with different above said electrode combinations may cause capture of different areas of the LV that are distant to the selected anodal electrode.

Preferably, the anodal stimulation pulse strength (pulse amplitude and/or pulse width) is user-programmable or can be automatically adjustable by the device. Generally, larger amplitude of anodal pacing can generate larger area of virtual cathode. Preferably, the anodal pacing strength is maintained so that on one hand, the anodal pacing alone can result in LV capture, whereas on the other hand, it does not result in cathodal capture of RV (particularly when the SVC and/or RV coil are used as cathode) or phrenic nerve stimulation. Note however, for CRT with simultaneous bi-ventricular pacing (i.e., VV delay 0 ms), the simultaneous LV anodal capture and RV cathodal capture is accepted.

Now consider the cathodal stimulation that immediately follows the above said anodal stimulation. In one embodiment, the cathodal pacing is delivered by selecting the LV-TIP electrode as the cathode. In another embodiment, the cathodal pacing is delivered by selecting the LV-RING electrode as the cathode. In both embodiments, the anode can be selected from a plurality of electrodes, including but not limited to, the LV-RING, the device can IMD-CASE, the SVC-COIL, the RV-COIL, or the combined SVC-RV coils.

Different combinations of above said electrodes can form different spatial vectors for the cathodal pacing. In a preferred embodiment, the pacing vector used for the cathodal stimulation is different than that used for the anodal stimulation, so that the virtual anode generated by the cathodal pacing does not overlay with the virtual cathode generated by the anodal pacing. For example, in one embodiment, the anodal pacing is delivered between LV-RING electrode (anode) and the device can IMD-CASE (cathode), and the cathodal pacing is delivered between the LV-TIP electrode (cathode) and the LV-RING electrode (anode). In another embodiment, the anodal pacing is delivered between the LV-TIP electrode (anode) and the combined SVC-RV coils (cathode), and the cathodal pacing is delivered between the LV-TIP electrode (cathode) and the device can IMD-CASE (anode). Evidently, other configurations for the anodal pacing and cathodal pacing can be similarly programmed.

Preferably, the cathodal pacing strength (pulse amplitude and/or pulse width) is user-programmable or can be automatically adjustable by the device. Generally, larger amplitude of cathodal pacing may capture a larger area of myocardial area and reduce the conduction time from LV to RV. Preferably, the cathodal pacing strength is maintained so that on one hand, the cathodal pacing alone can result in LV capture, whereas on the other hand, it does not result in anodal capture of RV (particularly when the SVC and/or RV coil are used as anode) or phrenic nerve stimulation. Note however, for CRT with simultaneous bi-ventricular pacing (i.e., VV delay 0 ms), the simultaneous LV cathodal capture and RV anodal capture could be accepted.

In another embodiment, an additional anodal pacing pulse is delivered before the cathodal pacing. That is, two anodal pacing pulses are applied before applying the cathodal pacing. Preferably, the first anodal pacing and the second anodal pacing use different pacing vectors so that the generated virtual cathodes are separated in space. For example, the first anodal pacing is delivered between the LV-RING electrode (anode) and the RV coil (cathode), the second anodal pacing is delivered between the LV-TIP electrode (anode) and the device can IMD-CASE (cathode), and the following cathodal pacing is delivered between the LV-TIP electrode (cathode) and the LV-RING electrode (anode). Evidently, other polarity configurations can be similarly programmed.

Yet in a further embodiment, dual-site capture can be achieved by anodal bipolar pacing alone, i.e., without the following cathodal pacing. Specifically, the LV anodal pacing is delivered between the LV-TIP electrode (anode) and the LV-RING electrode (cathode). The virtual cathode generated by the anodal bipolar pacing can capture the myocardial site that is distant to the LV-TIP electrode, whereas the LV-RING electrode can depolarize the local myocardial cells.

The main purpose of the switch polarity pacing is to nearly simultaneously depolarize multiple areas of the LV. By this means, larger myocardial volume can be activated by multiple activation waves, which may extend beyond the region of myocardial infarction or conduction block, thus improving the intra-ventricular synchrony and hemodynamic performance of the LV. Another benefit of the switch polarity pacing is that it can minimize the risk of arrhythmia. The anodal pacing depolarizes the remote myocardial site while hyperpolarizing the local myocardial site. The immediately following cathodal pacing captures the local myocardial site, rendering it refractory to further depolarization, and pre-venting the formation of reentry circuit.

As described above, the pacing strength of the anodal pacing can be adjusted to affect the size of the virtual cathode. Also for both anodal pacing and cathodal pacing, the cathode and anode can be respectively selected from a plurality of electrodes to form different pacing vectors, which can capture different areas of the heart. According to this invention, the optimization of pacing strength and pacing vectors are performed to maximize the improvement of the cardiac function.

In one embodiment, the optimization of pacing strength and pacing vectors are achieved during initial device implant or during device follow-up, when the ventricular function is manually assessed by various measures, including but are not limited to LV dP/dt, LV ejection fraction, LV wall motion dysynchrony index, etc., as known in the art.

In another embodiment, the optimization of pacing strength and pacing vectors are achieved automatically by the implant device. For example, one optimization target is to minimize the conduction time from the LV pace to the RV sense. Another optimization target is to minimize the duration of the QRS complex as measured by the surface ECG or intracardiac electrogram. Yet another optimization target is to maximize the myocardial contractility as measured by the unipolar impedance that is implemented by means of the impedance measuring unit 70. Yet a further optimization target is to maximize the stroke volume that can be correlated with the difference between end-systolic and end-diastolic intracardiac impedances. Other device-based optimization techniques using various hemodynamic sensors can also be used, as known in the art.

Although the switch polarity pacing described above is focused on the left ventricle, it should be understood that the same principles and methods also apply to the right ventricle. For heart failure patients with delayed right ventricular activation (e.g., the right bundle branch block) or with intra-RV dysynchrony, the switch polarity RV pacing can also be used to achieve multi-site RV capture, thus improving the RV function.

What is claimed is

1. A heart stimulator for left-ventricular pacing comprising:
   an electrode comprising a housing of an implantable device;
   an electrode comprising a coil;
   a left ventricular stimulation pulse generator connected to a single left ventricular electrode lead to stimulate a left ventricular myocardium and having one or more electrodes configured to deliver stimulation pulses to left ventricular myocardial heart tissue, said left ventricular stimulation pulse generator configured to generate and deliver at least one anodal and cathodal stimulation pulses of switchable polarity; and,
   a control unit connected to said left ventricular stimulation pulse generator and configured to control said left ventricular stimulation pulse generator to
     trigger generation of, and deliver stimulation pulses having a polarity controlled by said control unit, and to deliver supra-threshold stimulation pulses of opposite polarity comprising anodal and cathodal pulses, wherein said supra-threshold stimulation pulses are delivered between a different combination of two electrodes selected from said housing, coil and said one or more electrodes on said single left ventricular electrode lead,
   wherein the control unit is configured to control said left ventricular stimulation pulse generator so as to first deliver a first anodal stimulation pulse via a first combination of two electrodes that lead to capture a first left ventricular region, deliver a cathodal stimulation pulse via a second different combination of electrodes that immediately follows an anodal stimulation pulse to capture a second different left ventricular region, and deliver a second anodal pacing pulse before said cathodal pacing pulse via a third different electrode combination to capture a third different left ventricular region, and
   wherein the first anodal pacing pulse electrode combination and the second anodal pacing pulse electrode combination have no common electrode.

2. The heart stimulator of claim 1, wherein said single left ventricular electrode lead comprises a left ventricular tip electrode and said control unit is configured to select said left ventricular tip electrode as anode for said first anodal pacing or said second anodal pacing.

3. The heart stimulator according to claim 2 wherein said control unit is configured to control said left ventricular stimulation pulse generator so as to deliver said first and/or second anodal stimulation pulse having a strength that is selected so that the anodal pacing alone results in left ventricular capture, whereas the anodal pacing does not result in cathodal capture of a right ventricle or phrenic nerve stimulation.

4. The heart stimulator of claim 1, wherein said single left ventricular electrode lead comprises a left ventricular ring electrode and said control unit is configured to select said left ventricular ring electrode as anode for said first anodal pacing or said second anodal pacing.

5. The heart stimulator of claim 1, wherein said single left ventricular electrode lead comprises a left ventricular tip electrode and said control unit is configured to select said left ventricular tip electrode as anode for said first-anodal pacing or said second anodal pacing;
   wherein said single left ventricular electrode lead comprises a left ventricular ring electrode and said control unit is configured to select said left ventricular ring electrode as anode for said first anodal pacing or said second anodal pacing; and,
   wherein said heart stimulator comprises or is connected to further electrodes other than said left ventricular tip electrode or said left ventricular ring electrode, and said control unit is configured to select one of said further electrode as cathode for said first anodal pacing or said second anodal pacing.

6. The heart stimulator of claim 5, wherein said one of said further electrodes that act as a cathode for said first or second anodal pacing comprise one or more of:
   an electrically conducting part of a heart stimulator's housing,
   a coil electrode configured to be placed in a superior vena cava (SVC),
   a coil electrode configured to be placed in a right ventricle,
   or a combination of said coil electrode configured to be placed in the superior vena cava (SVC) and said coil electrode configured to be placed in the right ventricle.

7. The heart stimulator according to claim 1, wherein said single left ventricular electrode lead comprises a left ventricular ring electrode and said control unit is configured to select said left ventricular ring electrode as cathode for cathodal pacing.

8. The heart stimulator according to claim 7 wherein said control unit is configured to control said left ventricular stimulation pulse generator so as to deliver a cathodal stimulation pulse having a strength that is selected so that the cathodal pacing alone results in left ventricular capture, whereas the cathodal pacing does not result in anodal capture of the right ventricle or phrenic nerve stimulation.

9. The heart stimulator according to claim 1, wherein said single left ventricular electrode lead comprises a left ventricular tip electrode and said control unit is configured to select said left ventricular tip electrode as cathode for cathodal pacing.

10. The heart stimulator of claim 1,
wherein said single left ventricular electrode lead comprises a left ventricular ring electrode and said control unit is configured to select said left ventricular ring electrode as cathode for cathodal pacing;
wherein said single left ventricular electrode lead comprises a left ventricular tip electrode and said control unit is configured to select said left ventricular tip electrode as cathode for cathodal pacing; and,
wherein said heart stimulator comprises or is connected to further electrodes other than said left ventricular tip electrode or said left ventricular ring electrode, and said control unit is configured to select one of said further electrode as anode for cathodal pacing.

11. The heart stimulator of claim 10, wherein said one of said further electrodes that act as anode for cathodal pacing comprise one or more of:

an electrically conducting part of a heart stimulator's housing,
a coil electrode configured to be placed in a superior vena cava (SVC),
a coil electrode configured to be placed in a right ventricle, or a combination of said coil electrode configured to be placed in the superior vena cava (SVC) and said coil electrode configured to be placed in the right ventricle.

12. The heart stimulator according to claim 1 wherein said control unit is configured to control said left ventricular stimulation pulse generator so as to deliver said first and second anodal stimulation pulses via at least one electrode on said single left ventricular electrode lead and to deliver a cathodal stimulation pulse via an electrode on said single left ventricular electrode lead.

13. The heart stimulator of claim 12, wherein said control unit is configured to control said left ventricular stimulation pulse generator so that the first anodal stimulation pulse is delivered between a left ventricular ring electrode that acts as anode and a right ventricular coil electrode that acts as cathode, the second anodal stimulation pulse is delivered between a left ventricular tip electrode that acts as anode and an electrically conducting housing of a heart stimulator that acts as cathode, and a following cathodal stimulation pulse is delivered between the left ventricular tip electrode that acts as cathode and the left ventricular ring electrode that acts as anode.

14. The heart stimulator of claim 1 wherein
said anodal stimulation pulses and said cathodal stimulation pulse have supra-threshold stimulation strength that is sufficient to cause capture of the left ventricular myocardium.

* * * * *